United States Patent [19]

Kunkee et al.

[11] 4,374,859
[45] Feb. 22, 1983

[54] METHOD FOR REDUCING FUSEL OIL IN ALCOHOLIC BEVERAGES AND YEAST STRAIN USEFUL IN THAT METHOD

[75] Inventors: Ralph E. Kunkee; S. Richard Snow, both of Davis; Craig Rous, Lodi, all of Calif.

[73] Assignee: The Regents of The University of California, Berkeley, Calif.

[21] Appl. No.: 166,546

[22] Filed: Jul. 7, 1980

[51] Int. Cl.³ ........................ C12G 3/12; C12P 7/06; C12N 15/00; C12N 1/18
[52] U.S. Cl. ........................................ 426/14; 426/15; 426/62; 426/494; 435/161; 435/172; 435/255; 435/942
[58] Field of Search ............... 435/172, 255, 256, 161, 435/162, 163, 164, 165, 942, 60, 62; 426/494, 11, 14, 15

[56] References Cited

U.S. PATENT DOCUMENTS 2,663,667 12/1953 Scott .................................... 435/161
4,035,515 6/1977 Cunningham ......................... 426/14
4,318,929 3/1982 Clement et al. ...................... 435/172

OTHER PUBLICATIONS

Ingraham et al., The Formation of Higher Aliphatic Alcohols by Mutant Strains of *Saccharomyces cerevisiae*, Archives of Biochemistry and Biophysics, 88, 157–166, (1960).
Pelczar et al., *Microbiology*, McGraw-Hill Co., N.Y., N.Y., 1972, pp. 301, 304 and 305.

*Primary Examiner*—Raymond N. Jones
*Assistant Examiner*—John E. Tarcza
*Attorney, Agent, or Firm*—Fliesler, Dubb, Meyer & Lovejoy

[57] ABSTRACT

A method and microorganism are set out for producing a fermentation product which contains ethanol but has a lower than usual fusel oil content. The mutant microorganism is of the genus Saccharomyces or Torulaspora.

10 Claims, No Drawings

METHOD FOR REDUCING FUSEL OIL IN ALCOHOLIC BEVERAGES AND YEAST STRAIN USEFUL IN THAT METHOD

DESCRIPTION

Technical Field

This invention relates generally to the production of alcohol (ethanol) with reduced fusel oil (higher alcohols) content from a yeast fermentation process, and more particularly to the production of ethanol with low fusel oil content for the preparation of distilled beverage spirits.

Background Art

The fermentation of carbohydrates to produce ethanol, utilizing strains of various microorganisms (i.e., various yeast strains), is very well known. Such diverse carbohydrate-containing food materials as corn, grapes, apples, rye, potatoes, berries, rice and wheat are utilized for producing ethanol in this manner. Further, it is common to distill the ethanol produced by such fermentation so as to provide a distilled spirit for brandy, whiskey, vodka, gin, liqueurs, wine spirits for dessert and appetizer wine fortification, and the like.

A problem arises when a fermentation product containing ethanol is distilled to produce distilled spirits: the fusel oil content, particularly the isoamyl alcohol content, is concentrated in the distilled spirit. Unfortunately, isoamyl alcohol has an objectionable burning, biting, flavor. Even when the concentration of isoamyl alcohol is below taste level, it and the other higher alcohols are sometimes said to have a deleterious effect upon the health of the person imbibing them. Highly efficient distillation can be used to reduce the higher alcohol content, but the added expense is considerable. Accordingly, it would be advantageous if the fusel oil content of distilled spirits could be reduced in a less expensive and simpler manner than is now often used.

It is known that certain leucine-requiring mutants of laboratory strains of yeast, which will not produce sufficient ethanol for commercially feasible distillation processes, produce only a trace of isoamyl alcohol. It is also known that some valine-requiring mutants produce markedly less isobutyl alcohol than do their parent strains. Such instances are discussed, for example, in an article entitled "The Formation of Higher Aliphatic Alcohols by Mutant Strains of *Saccharomyces cerevisiae*" by John L. Ingraham and James F. Guymon, Archives of Biochemistry and Biophysics, Volume 88, Number 1, 1960, pages 157–166. The particular yeast strains discussed in this article do not grow in media having an ethanol content greater than about 5% or 6% by volume. Hence, these strains are not suitable for the commercial production of ethanol from carbohydrates.

The commercially utilized wine yeast strains such as Montrachet (UCD Enology 522, ATCC 36025) will produce beverages with relatively high ethanol content, for example about 14% by volume, before the fermentation process stops. Such strains, however, produce the usual amounts of fusel oil. It would be desirable to have a strain capable of fermenting carbohydrates to relatively high ethanol concentrations, but which at the same time would produce a fermentation product that had reduced fusel oil content. Prior to the present invention such a strain was not available.

Disclosure of the Invention

In accordance with an embodiment of the present invention, a method is set out for producing a fermentation product containing ethanol which has a lower than usual fusel oil content. The method comprises fermenting a nutrient medium containing a suitable carbohydrate substrate with a mutant strain of the genus Saccharomyces or of a related genus (Torulaspora), which has a reduced ability to produce one of the fusel oils components [that is, n-propyl alcohol (n-propanol), isobutyl alcohol (2-methyl-1-propanol), optically active amyl alcohol (2-methyl-1-butanol), or isoamyl alcohol (3-methyl-1-butanol)] and which has the ability to produce a fermentation product with an ethanol content of at least about 8% by volume, and preferably at least about 10% by volume.

The invention is also directed to a microorganism having the desired properties for use in the just set out method.

Through utilizing a method and a mutant microorganism as discussed above, one can commercially ferment any of a number of starch or other carbohydrate-containing materials to form a fermentation product having a significantly reduced content of one of the higher alcohols, for example isoamyl alcohol. The amount of isoamyl alcohol or other higher alcohols present in a distillate prepared from the fermentation product will likewise be reduced.

Best Mode for Carrying out the Invention

In accordance with the present invention, a mutant microorganism is produced which can be used under normal fermentation conditions in a commercial fermentation process to convert a carbohydrate substrate to ethanol with the resulting fermentation product having a reduced amount of fusel oil, that is a reduced amount of higher alcohols such as n-propyl, isobutyl, optically active amyl, or isoamyl alcohols. It is particularly desirable that the product have a low amount of isoamy alcohol.

Generally, the microorganism will be a yeast and preferably a yeast of the genus Saccharomyces or of the genus Torulaspora. It is particularly preferred that the microorganism be a mutant form of a commercial fermentation yeast strain utilized to produce ethanol in an amount of at least about 8% by volume in the fermentation product. Among the yeasts which are particularly useful are *Saccharomyces cerevisiae, Saccharomyces cerevisiae* var. elliopsoideus, *Saccharomyces beticus, Saccharomyces bayanus, Saccharomyces carlsbergensis, Saccharomyces uravum, Saccharomyces vini, Saccharomyces oviformis, Saccharomyces chevalieri, Saccharomyces fermentati,* and *Saccharomyces rosei.* According to the latest yeast nomenclature, all of these yeast species, except for the last two, are more properly classified as species *Saccharomyces cerevisiae* Hansen, while the last two are more properly classified as *Torulaspora delbrueckii* Lindner ("A Guide to Identifying and Classifying Yeasts," by J. A. Barnett, R. W. Payne, and D. Yanow, Cambridge University Press, 1979).

The carbohydrates which can be utilized in accordance with the method of the present invention include any of the starch or sugar-containing materials normally fermented to form ethanol, for example, grapes, any of various grains, potatoes or certain other tuberous vegetables, any of various berries, any of various fruits, and the like. The fermentations are normally run under the usual fermentation conditions used with a non-mutant strain of the same yeast. When starch is used as a substrate it must first be chemically, biologically or enzymatically converted ("malted") to sugar.

It is preferred that the total fusel oil content in the fermentation product be reduced to about 80% of the total fusel oil content produced by the parent strain. It is particularly preferred that the isoamyl alcohol content in the fermentation product be no more than about 60%, and more preferably no more than about 50%, of that produced by the parent strain of the same microorganism. It is to be noted that isoamyl alcohol will generally be present in four to five times the quantity of any of the other fusel oils. Hence, even if the amounts of some of the other fusel oils are slightly increased while the isoamyl alcohol content is decreased, the overall effect will be a reduction in total fusel oil content.

In accordance with the present invention, the fermentation product will normally be distilled to produce a distillate having an ethanol content of at least about 70% and in which the fusel oil will be concentrated over that in the fermentation product. However, because of the reduced fusel oil content in the fermentation product, the distillate will have less fusel oil content than that produced utilizing the parent strain of the same microorganism during the fermentation process. Thus, it is not necessary to utilize extremely efficient, but expensive to build and operate, distillation apparatus.

While not meaning to be bound by any theory as to the production of a proper mutant strain having the desired characteristics set out above, it is noted that it may be difficult to obtain the desired mutation in strains of yeast used in commercial ethanol fermentations because such yeast strains are not normally haploid. Also, because such commercial yeast strains often sporulate poorly, have poor viability of spores, and have poor growth of spore clones, it is preferable to use a derivative strain selected from one of the commercial strains which does not display these undesirable characteristics. The particular strain of Montrachet yeast which was used in these experiments was derived from the commercial Montrachet strain (*Saccharomyces cerevisiae*, UCD Enology 522, ATCC 36025), as described in the article entitled "Toward Genetic Improvement of Wine Yeast", by Richard Snow, American Journal of Enology and Viticulture, Volume 30, Number 1, 1979, pages 33–37, and was identified as strain UCD Enology 552X (ATCC 42512) submitted to ATCC May 5, 1980. It is probably diploid.

It was decided that it would be advantageous to treat a sporulated culture of strain 552X with the mutagen, in the expectation that desirable mutation might be induced in the haploid spores present in the culture, so making isolation of the desired mutation easier. In the actual experiments run, both unsporulated diploid cells and haploid spores were present in the sample which was treated with the mutagen. The particular mutagen utilized was ethyl methanesulfonate. The method of treatment with this mutagen was as described in an article entitled "Mutants of Yeast Sensitive to Ultraviolet Light", by Richard Snow, Journal of Bacteriology, Volume 94, Number 3, 1967, pages 571–575. After mutagen treatment the cells were carried through two cycles of nystatin counterselection treatment, as described in the article entitled "An Enrichment for Auxotrophic Yeast Mutants Using the Antibiotic 'Nystatin'," by Richard Snow, Nature, Volume 211, Number 5045, 1966 pages 206–207. The desired mutants (i.e., leucine mutants) were identified as those cells which would not grow unless the medium was supplemented with the amino acid leucine. Stable, genetically uniform mutant strains were derived from the original mutant strains by the same procedure as was used to derive strain 522X (ATCC 42512).

EXAMPLE

A mutated form of Montrachet yeast, namely ATCC 20602, was produced as described above by utilization of the mutagen ethyl methanesulfonate upon strain 522X (ATCC 42512) which was derived from commercial Montrachet yeast (UCD Enology 552, ATCC 36025). On testing, it was found that the mutant strain required leucine and produced lowered amounts of isoamyl alcohol when used in an ethanol fermentation process.

In the fermentation process, a grape juice inoculum with an actively growing mutant yeast population was added to a fermentation medium composed of grape juice extracted from Chenin blanc grapes. The amount of inoculum represented 4% of the final fermentation medium volume. The fermentation was carried out under essentially anerobic conditions for a time of 60 days at an ambient temperature of 16.5° C. At the end of this time, the ethanol content of the fermentation medium had reached 12.1%. The fermentation product was analyzed for n-propyl, isobutyl, optically active amyl, and isoamyl alcohol. The results are summarized in Table 1 below.

An otherwise identical fermentation was carried out utilizing the non-mutated (parent) strain of the same Montrachet yeast, namely strain 552X, ATCC 42512. The results of that fermentation as to the contents of n-propyl, isobutyl, optically active amyl and isoamyl alcohols are likewise set out in Table 1 below.

TABLE 1

| Yeast strain | Ethanol (% by volume) | n-propyl alcohol | | |
|---|---|---|---|---|
| Parent (ATCC 42512) | 12.2 | 3.58 | | |
| Mutant (ATCC 20602) | 12.1 | 4.71 | | |
| Yeast strain | Isobutyl alcohol | Optically active amyl | Isoamyl alcohol | Total higher alcohols |
| Parent (ATCC 42512) | 3.91 | 4.36 | 18.27 | 30.12 |
| Mutant (ATCC 20602) | 6.61 | 5.02 | 8.63 | 24.97 |

The above results show that the isoamyl alcohol content of the fermentation product utilizing the mutated yeast strain was only about 47.2% of that which resulted when the non-mutated parent strain was used. The weight ratio of isoamyl alcohol to ethanol was below about $1 \times 10^{-3}$ with the mutated yeast strain whereas it was about $2 \times 10^{-3}$ with the non-mutated strain. Thus, the undesirable isoamyl alcohol was significantly reduced in the fermentation product, as was the total higher alcohol content.

Industrial Applicability

The present invention is useful for converting any carbohydrate which is normally fermentable into ethanol into an ethanol-containing fermentation product having a reduced fusel oil content. The invention is particularly useful when the fermentation product is distilled to provide a distillate having an increased ethanol content and an increased fusel oil content, over that which is present in the fermentation product.

Other aspects, objects, and advantages of this invention can be obtained from a study of the disclosure and the appended claims.

We claim:

1. A method for producing ethanolic fermentation products of low fusel oil content, comprising:

fermenting a nutrient medium having a fermentable carbohydrate substrate with a diploid mutant of a Saccharomyces or a Torulaspora species, which has a reduced ability to produce fusel oil during the fermenting, said fusel oil being selected from a group consisting of n-propyl, isobutyl, optically active amyl, and isoamyl alcohols, said microorganism having the ability to produce a fermentation product having an ethanol content of at least 8%.

2. A method as in claim 1, further including: distilling the fermentation product to produce a distillate having an ethanol content of at least about 70%.

3. A method as in claim 1, wherein said microorganism is a strain of Saccharomyces cerevisiae Hansen.

4. A method as in claim 3, wherein said strain comprises Saccharomyces cerevisiae ATCC 20602.

5. A method as in claim 1, wherein said fusel oil is isoamyl alcohol and wherein said mutant produces said fermentation product having an isoamyl alcohol content of no more than about 60% of the isoamyl content in a fermentation product produced by a non-mutated strain of the same microorganism.

6. A method as in claim 5, wherein said microorganism is a strain of Saccharomyces cerevisiae Hansen.

7. A method as in claim 6, wherein said microorganism comprises Saccharomyces cerevisiae ATCC 20602.

8. A biologically pure culture of a diploid microorganism of the genus Saccharomyces or Torulspora characterized by having capabilities comprising:

fermenting, under optimal conditions, a carbohydrate substrate to a fermentation product having at least 8% by volume of ethanol and having a weight ratio of isoamyl alcohol to ethanol of no more than about $1 \times 10^{-3}$.

9. A microorganism as in claim 8, wherein said microorganism is a strain of Saccharomyces cerevisiae Hansen.

10. A microorganism as in claim 8, wherein said microorganism comprises Saccharomyces cerevisiae ATCC 20602.

* * * * *